(12) United States Patent
Kain

(10) Patent No.: US 12,016,839 B2
(45) Date of Patent: Jun. 25, 2024

(54) PROCESS FOR PRODUCING A VEGAN CANNABINOID CHEWY

(71) Applicant: Dirk Kain, Chattanooga, TN (US)

(72) Inventor: Dirk Kain, Chattanooga, TN (US)

( * ) Notice: Subject to any disclaimer, the term of this patent is extended or adjusted under 35 U.S.C. 154(b) by 13 days.

(21) Appl. No.: 17/836,089

(22) Filed: Jun. 9, 2022

(65) Prior Publication Data

US 2022/0395484 A1 Dec. 15, 2022

Related U.S. Application Data

(60) Provisional application No. 63/209,120, filed on Jun. 10, 2021.

(51) Int. Cl.
| | | |
|---|---|---|
| A61K 31/352 | (2006.01) | |
| A61K 9/00 | (2006.01) | |
| A61K 31/05 | (2006.01) | |
| A61K 47/12 | (2006.01) | |
| A61K 47/26 | (2006.01) | |
| A61K 47/36 | (2006.01) | |

(52) U.S. Cl.
CPC .......... *A61K 31/352* (2013.01); *A61K 9/0056* (2013.01); *A61K 31/05* (2013.01); *A61K 47/12* (2013.01); *A61K 47/26* (2013.01); *A61K 47/36* (2013.01)

(58) Field of Classification Search
CPC .................................................. A61K 9/0056
See application file for complete search history.

(56) References Cited

U.S. PATENT DOCUMENTS

| | | |
|---|---|---|
| 2016/0199299 A1 | 7/2016 | Uren |
| 2020/0108018 A1 | 4/2020 | Shadurin et al. |
| 2020/0138705 A1* | 5/2020 | Wan .................... A61K 36/232 |
| 2020/0170950 A1 | 6/2020 | Adair et al. |
| 2020/0261406 A1 | 8/2020 | Muscarella |
| 2020/0268652 A1 | 8/2020 | Hess |
| 2021/0401736 A1* | 12/2021 | Wan ...................... A61K 47/10 |

OTHER PUBLICATIONS

Hydrocolloids Primer Pearson https://www.cookingissues.com/index.html%3Fp%3D1247.html (Year: 2019).*
Agar Agar in Vegan Jelly Candy: The Application and Production Method Gino Gums and Stabilizers https://gumstabilizer.com/agar-agar-in-vegan-jelly-candy/ (Year: 2020).*

* cited by examiner

*Primary Examiner* — Jeffrey S Lundgren
*Assistant Examiner* — Eric Tran
(74) *Attorney, Agent, or Firm* — COATS & BENNETT, PLLC

(57) ABSTRACT

A process for producing a vegan cannabinoid chewy wherein the process entails mixing a cannabinoid compound with a sugar solution, pectin mixture, and agar mixture.

3 Claims, No Drawings

PROCESS FOR PRODUCING A VEGAN CANNABINOID CHEWY

RELATED APPLICATIONS

This application claims priority to U.S. Provisional Application No. 63/209,120, filed Jun. 10, 2021, the disclosure of which is incorporated herein by reference in its entirety.

FIELD OF THE INVENTION

The present invention relates to processes for producing cannabinoid edible or chewy products.

BACKGROUND

In the cannabis industry, an important aspect of preparing a commercial product is the ability to formulate cannabinoids and other cannabis-derived compounds in a desirable form for human consumption. Specifically, cannabinoids and other cannabis-derived compounds present challenges for preparing desirable consumer products, particularly edible food stuffs and chewies. Cannabinoids, including many cannabinoid extracts and oils, are generally insoluble in water. This makes it difficult to produce food products and is especially challenging in obtaining desirable concentrations of cannabinoids in these products.

The therapeutic effects of cannabis have been known for many years. Consumption of compounds found in cannabis is known to have therapeutic effects for many disorders and ailments including, for example, eating disorders, sleep disorders, and anxiety issues. The active components of cannabis are referred to as cannabinoids. There are many forms of cannabinoids in cannabis plants. One of the most known cannabinoids is tetrahydrocannabinol (THC) and cannabidiol (CBD). There are others. In the cannabis plant, these cannabinoids are mostly in an acid form. For many therapeutic applications, cannabinoids are heat treated prior to being incorporated into a consumable product to effect thermal decarboxylation of the cannabinoids, which is sometimes referred to as activation.

There is a need for a marketable cannabinoid consumable that is effective. One possibility is a cannabinoid chewy. However, providing a marketable cannabinoid chewy is quite challenging for a number of reasons. First, it is important that the cannabinoid chewy be heat stable and shelf stable. Further, it is important that the chewy maintain its integrity during initially chewing. Often chewy products have their integrity compromised because the process for producing them is flawed or something in the confectionery science, such as pH, moisture content, water activity, dexterous equivalency, etc. have been overlooked. Moreover, many chewable products are difficult to chew or are so porous that they lack sufficient integrity during the initial chewing phase.

Therefore, there has been and continues to be a need for a cannabinoid chewy that is produced in a process that overcomes these shortcomings discussed above.

SUMMARY OF THE INVENTION

The present invention entails a process for producing a cannabinoid chewy that is heat and shelf stable and which is easy to chew and which can be effortlessly consumed by those who are elderly or have difficulty chewing or digesting cannabinoid edibles. At the same time, the process produces a cannabinoid chewy that imparts an enjoyable and flavorful experience for those that are consuming the chewy.

The process of the present invention produces a cannabinoid chewy that is heat and shelf stable and has a relatively long life. Moreover, the process is designed to produce a vegan cannabinoid chewy that is easy to chew and initially does not break apart easily. In this regard, the process is designed such that in the initial phase of chewing and consuming the chewy, the chewy maintains its integrity but after being subjected to initial chewing, the chewy breaks apart and dissipates quickly which results in a quicker onset of the cannabinoid effects while still maintaining full flavor.

In one embodiment of the present invention, the process of producing the cannabinoid chewy includes mixing at least one cannabinoid compound or other cannabis-derived compound with pectin and agar. Pectin is a soluble gelatinous polysaccharide that is present in ripe fruits and is extracted for use as a setting agent in jams and jellies. Agar, on the other hand, is a gelatinous substance obtained from various kinds of red seaweed and used in biological culture media and as a thickener in foods. As discussed below, the pectin and agar are prepared in a particular manner. First, a sugar slurry preparation is prepared. In addition, a pectin solution is prepared. After the pectin preparation is produced, it is introduced into the sugar slurry preparation. Further, the process entails preparing a particular agar preparation. Once the agar preparation is prepared, it too is introduced into the sugar slurry preparation. Finally, to adjust the pH, an acidic reagent, such as citric acid, is introduced into the total mixture sufficiently to result in a final pH of approximately 3.90-4.10.

Other objects and advantages of the present invention will become apparent and obvious from a study of the following description.

DESCRIPTION OF PREFERRED EMBODIMENT

The present invention is a process for producing a vegan cannabinoid chewy. The basic constituents of the cannabinoid chewy is a sugar slurry, pectin, agar and at least one cannabis-derived compound, such as a cannabinoid compound. The term "cannabinoid compound" is used herein to mean any cannabis-derived compound. Both pectin and agar are individually incorporated into a solution by a particular process. This yields a pectin solution and an agar solution that are mixed or combined with a sugar slurry and a cannabinoid compound to yield the cannabinoid chewy having the desirable properties and characteristics discussed above.

The process includes preparing a sugar slurry solution. Various constituents and processes can be used to prepare the sugar slurry solution. In one example, the sugar slurry solution is principally made up of selected amounts of sugar, corn syrup, and sorbitol (added for texture and to combat water activity). The sugar, corn syrup, and sorbitol mixture are heated and stirred until it reaches a temperature of approximately 260°–265° F. The sugar slurry solution is maintained within that temperature range until the pectin solution and the agar solution are mixed therewith.

Now turning to the pectin preparation, the process includes employing a selected pectin to glucose ratio, as well as a selected pectin to citric acid ratio. Pectin mixtures are commercially available and are typically sold in the form of a powder. Typically, the pectin powder includes pectin, glucose (or sucrose or dextrose) and citric acid. In practice, a sufficient amount of the pectin powder is employed to yield a consistent gelling agent. As described below, once the cannabinoid compound, along with the sugar slurry solution, the pectin solution and the agar solution have been combined, citric acid is reintroduced to establish a final pH between approximately 3.90 and 4.10.

The pectin powder is mixed with water. The mixture of pectin powder and water will result in a pH elevation as pectin and water when selectively mixed have a pH at around 2.10-2.25. Thereafter, baking soda or sodium bicarbonate is added to the pectin and water mixture. The amount of sodium bicarbonate added is calculated to increase the pH of the mixture to 5.25-5.50. This will prevent the slurry from congealing too quickly. Once the sodium bicarbonate has been added to the pectin and water mixture, the resulting mixture is stirred at a specific temperature and for a time period until a selected sugar content or dissolved solids content is reached. Thereafter, the mixture of pectin, water and sodium bicarbonate is stirred at 225-240 degrees F. for approximately 4-5 minutes. After this, the temperature of the mixture is dropped to 160°-170° F. for an additional four minutes. This prepares the pectin preparation or the pectin solution.

The pectin solution is then added to the sugar slurry solution discussed above. This mixture is stirred until the foam subsides and in a preferred embodiment, the stirring is continued for a selected period of time.

To prepare the agar solution, a selected amount of agar is added and mixed with water. In one embodiment, the amount of agar mixed with the water is calculated to be approximately 30 grams of agar to every seven ounces of water. Various forms of agar can be used, but in this example the agar is in a powder form and is stirred in the water until the water is entirely saturated with the agar (usually takes 20-25 minutes with occasional stirring). This mixture is heated to 230°–245° F. When the mixture starts to boil and create bubbles, the mixture is stirred vigorously until a selected thickness and consistency has been achieved. At this time, the temperature of the mixture is dropped to 160°–170° F. and is continued to be stirred.

Thereafter, the agar solution just described is added and mixed with the sugar slurry solution and the pectin solution mixture.

Finally, citric acid is introduced into the final mixture to adjust the pH to approximately 3.90-4.10.

Prior to adding the citric acid, the cannabis-derived compound is added and mixed with the final mixture. In one embodiment, the cannabis-derived compound comprises a cannabinoid solution that, in one example, can be made up of a cannabinoid distillate or isolate and refined coconut oil. This cannabinoid solution is mixed with the final mixture and thoroughly stirred for approximately 90-120 seconds. Thereafter, flavoring and coloring can be added and stirred into the final mixture. In some embodiments, the citric acid discussed above is added at this point.

This produces a hot gummy or chewy material which is poured or deposited into molds. The molds are scraped to smooth out to remove any excess gummy matter. The hot gummy material will set in the molds, in one example, for approximately 20 to 24 hours. After this, the gummies or chewies are popped out of the molds, steamed and tumbled in sugar. Thereafter, the gummies or chewies are dumped onto trays to cure for approximately 5-7 days. Now the gummies are ready to be packaged, batched and delivered to customers.

There are a number of important differences between the process described above and conventional processes for producing chewy products. One of the differences lies in the preparation of the pectin solution. In most confectionary environments, the pectin powder is initially mixed with glucose or corn syrup or the powder is added directly to the sugar slurry solution. In the process of the present invention, the process entails a pH neutralization step that includes mixing the pectin powder with water and sodium bicarbonate. In terms of the agar solution, in most confectionary environments, the conventional practice is to mix pectin and gelatin to achieve a chewy consistency of a "gummy". This, of course, is not a vegan product as is the present invention. In the present process, only pectin is used without gelatin. In most conventional processes, if the goal is to produce a vegan product, these processes typically only use pectin and not agar. If agar is used, the agar powder is added to the sugar slurry solution. That is to be contrasted with the process of the present invention where agar is first fully dissolved in water and then brought to a boil and stirred. Thereafter, the mixture is added to the sugar and pectin mixture.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A process for producing a vegan cannabinoid chewy, comprising:
   a. preparing a sugar slurry comprising sugar, corn syrup and sorbitol and heating the sugar slurry to a temperature of approximately 260°-265° F.;
   b. forming a pectin mixture by:
      i. mixing a pectin powder with water and sodium bicarbonate wherein a sufficient amount of sodium bicarbonate is added to the pectin mixture to yield a pH of approximately 5.25-5.50;
      ii. stirring the pectin mixture while maintaining the pectin mixture at a temperature of approximately 225° to approximately 240° F.;
      iii. after stirring the pectin mixture at the temperature of approximately 225° to approximately 240° F., reducing the temperature of the pectin mixture to approximately 160° to approximately 170° F.;
   c. forming an agar mixture by:
      i. mixing agar in a powder form with water at a rate of approximately 4.3 grams of agar per ounce of water;
      ii. heating the agar mixture to a temperature of approximately 230° to approximately 245° F.;
      iii. reducing the temperature of the agar mixture to approximately 160° to approximately 170° F.;
   d. mixing the pectin mixture with the sugar slurry;
   e. mixing the agar mixture with the sugar slurry;
   f. wherein mixing the pectin mixture and agar mixture with the sugar slurry forms a sugar-pectin-agar mixture;
   g. mixing a cannabinoid compound with the sugar-pectin-agar mixture to form a product mixture;
   h. adding citric acid to the product mixture to adjust the pH of the final mixture to approximately 3.90 to approximately 4.10;
   i. wherein the product mixture produces a gummy or chewy vegan product that is poured into molds; and
   j. wherein the gummy or chewy vegan product sets in the molds for a selected period of time after which the gummy or chewy vegan product is popped out of the molds.

2. The process of claim 1 wherein after the gummy or chewy vegan product is popped out of the molds, the gummy or chewy vegan product is steamed and tumbled in sugar.

3. The process of claim 1 wherein the cannabinoid compound comprises a cannabinoid distillate or isolate and refined coconut oil.

* * * * *